(12) United States Patent
Gaon

(10) Patent No.: US 6,281,500 B1
(45) Date of Patent: Aug. 28, 2001

(54) DETECTION AND MEASUREMENT OF COLD EMULSION ADHESIVES APPLIED TO A SUBSTRATE

(75) Inventor: Martin A. Gaon, Merrick, NY (US)

(73) Assignee: Nordson Corporation, Westlake, OH (US)

( * ) Notice: Subject to any disclaimer, the term of this patent is extended or adjusted under 35 U.S.C. 154(b) by 0 days.

(21) Appl. No.: 09/213,837

(22) Filed: Dec. 17, 1998

(51) Int. Cl.[7] .................................................. G01N 21/35
(52) U.S. Cl. ........................................................ 250/339.1
(58) Field of Search .......................................... 250/339.1

(56) References Cited

U.S. PATENT DOCUMENTS

| | | | | |
|---|---|---|---|---|
| 3,821,553 | * | 6/1974 | French | 250/339.1 |
| 5,049,216 | * | 9/1991 | Shead et al. | 156/64 |
| 5,406,082 | * | 4/1995 | Pearson et al. | 250/339.11 |
| 5,663,565 | | 9/1997 | Taylor . | |

FOREIGN PATENT DOCUMENTS

| | | |
|---|---|---|
| 3213335 C2 | 10/1983 | (DE) . |
| 0611608B1 | 12/1996 | (EP) . |
| 3-115838 | * 5/1991 | (JP) .................................. 250/339.1 |

OTHER PUBLICATIONS

Veritec GD 100 Glue Sensor, product announcement from Pafra, Inc. May 1998.

* cited by examiner

*Primary Examiner*—Constantine Hannaher
(74) *Attorney, Agent, or Firm*—Wood, Herron & Evans, LLP

(57) ABSTRACT

An apparatus and method for on line detection and measurement of cold emulsion adhesives, including a sensor of a presence of an adhesive on a substrate, the sensor being arranged to sense an amount of absorption of two specific wavelengths of near infrared energy by the adhesive, the two specific wavelengths including a first wavelength within an absorption band for water and a second wavelength outside an absorption band for water. The two sensed amounts are converted into two signals, a difference between the signals being indicative of the moisture content of the adhesive. If the two signals are the same, then the moisture content approximates zero. Otherwise, the difference is proportional to the moisture content.

17 Claims, 3 Drawing Sheets

DETECTION AND MEASUREMENT OF COLD EMULSION ADHESIVES APPLIED TO A SUBSTRATE

BACKGROUND OF THE INVENTION

1. Field of the Invention

The invention relates to an apparatus for on-line detection and measurement of cold emulsion adhesives applied to a substrate based on determining near infrared light energy absorption at two specific wavelengths, one being within an absorption band of water and the other being outside the absorption band of water.

2. Discussion of Related Art

On-line measurement of key glue-line characteristics of corrugated board is known from U.S. Pat. No. 5,663,565 (the '565 patent), entitled SYSTEM AND METHOD FOR THE ON-LINE MEASUREMENT OF KEY GLUE-LINE CHARACTERISTICS ON CORRUGATED BOARD and issued Sep. 2, 1997 and whose contents are incorporated herein by reference. According to its disclosure, the measurement signal is typically generated by either an infrared absorption sensor, which is used to measure the mass of moisture and/or starch in the glue-line, or an infrared pyrometer, which is used to measure the temperature of the glue-line. The chosen sensor is installed so as to measure the exposed glue-line prior to bonding of the medium with a liner. In addition, the disclosure reveals sensing isolated glue-based variations found in the sensor output signal that oscillate at a known fluting frequency of the corrugated board.

Variation in the sensor output signal that are not oscillating at the fluting frequency are canceled out, while those that are oscillating at the fluting frequency are isolated and amplified. An incremental amount of infrared radiation that is absorbed by starch and/or water in the glue-lines is isolated from the predominant, more random background absorption due to cellulose and water in the paper substrate. The amplitude of the extracted signal component, which reflects only starch and/or water in the glue, is then converted using empirically derived calibration constants into a final starch mass value. The output signal of an infrared absorption sensor, therefore, provides an improved on-line starch measurement for corrugators.

While the '565 patent mentions that to date no on-line glue measurement techniques have been successfully commercialized, the present inventors believe that have found a solution. The conventional problem with glue application on substrates lies with detection and correction of irregularities, which the '565 patent identifies and elaborates upon in some detail. However, the present inventors have devised a technique to discriminate the adhesive from its substrate and to quantify the moisture content of the substrate and adhesive to promote a more uniform glue application.

SUMMARY OF THE INVENTION

One aspect of the invention relates to an apparatus and method for on line detection and measurement of cold emulsion adhesives, including a sensor of a presence of an adhesive on a substrate, the sensor being arranged to sense an amount of absorption of two specific wavelengths of near infrared energy by the adhesive, the two specific wavelengths including a first wavelength within an absorption band for water a second wavelength outside an absorption band for water.

BRIEF DESCRIPTION OF THE DRAWINGS

For a better understanding of the present invention, reference is made to the following description and accompanying drawings, while the scope of the invention is set forth in the appended claims.

DESCRIPTION OF THE PREFERRED EMBODIMENT

Figure 1:
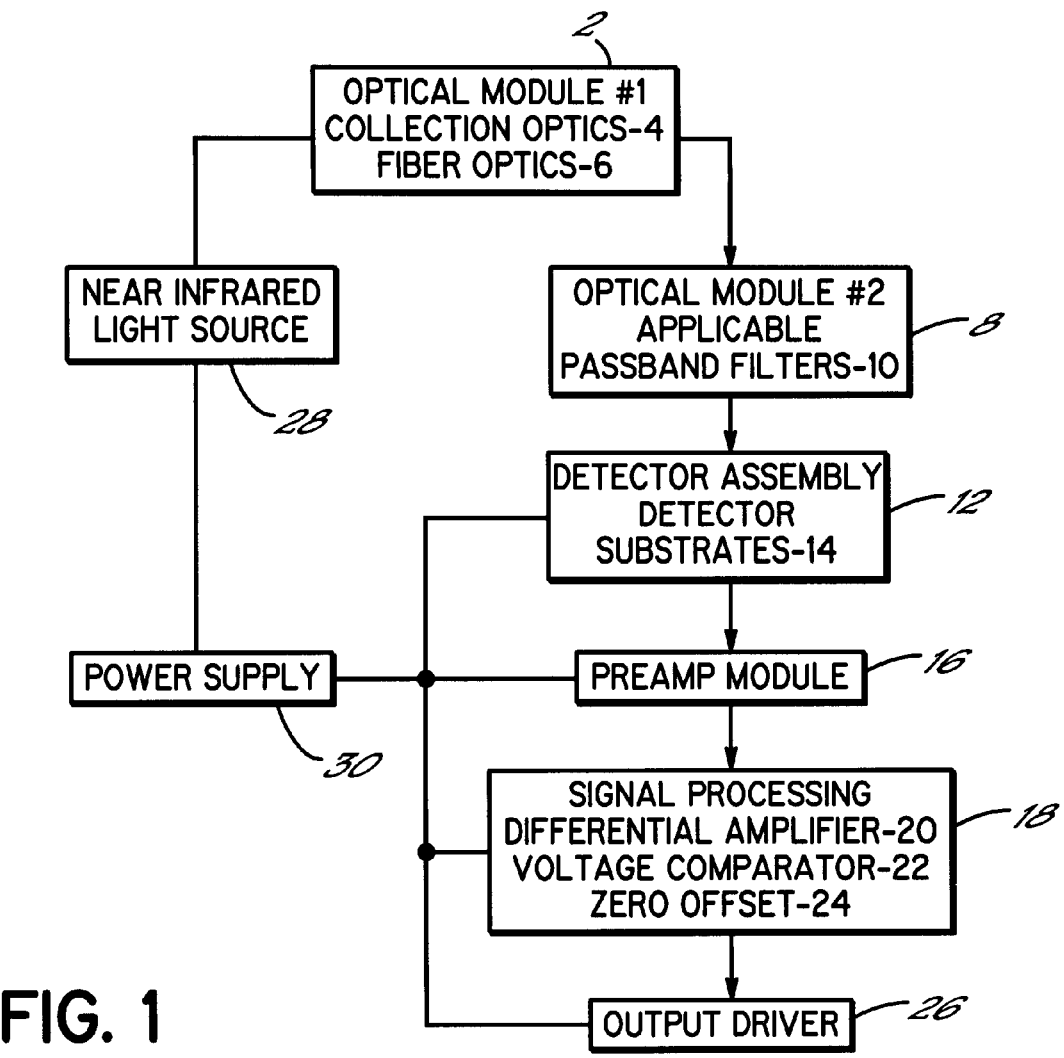
FIG. 1 is a functional block diagram for a glue detection apparatus in accordance with the invention.

Turning the drawing, FIG. 1 shows in block form an optical module 2 having collection optics 4 and fiber optics 6, an optical module 8 having applicable passband filters 10, a detector assembly 12 having detector substrates 14, a preamp module 16, signal processing electronics 18 having a differential amplifier 20, voltage comparator 22, zero offset 24 and an output driver 26. Also shown is a near infrared light source 28 and a power supply 30.

Figure 2:
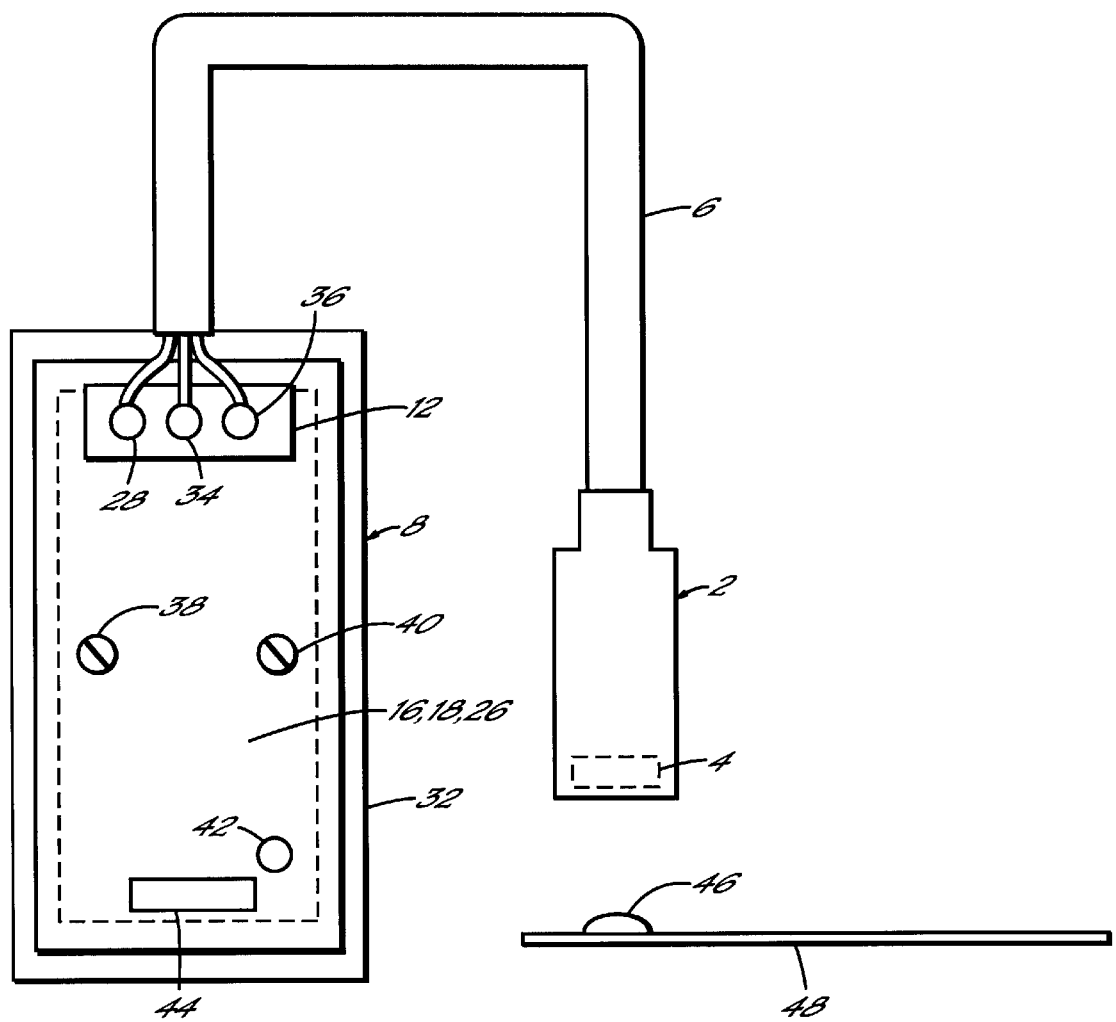
FIG. 2 is a schematic diagram of a glue detection apparatus that incorporates the functional block diagrams of FIG. 1 and of a carton substrate with glue applied.

FIG. 2 is the same glue detection apparatus as in FIG. 1. The optical module 2 is in the form of a lens assembly. The optical module 8 is in the form of a housing 32 containing the near infrared light source 28 in the form of the halogen light source, two filters and detectors 34, 36 of the passband filters 10 and detector substrates 14, the preamp module 16, the signal processing electronics 18, a zero adjustment control 38, a glue threshold adjustment control 40, an output indicator 42 and an input/output cable 44. Between the optic module 2 and the optic module 8 is trifurcated fiber optics 6.

The arrangement of FIG. 2 is used to detect water based adhesives 46 on a substrate 48, but the detection technique may be applied to non-aqueous adhesives on a substrate as well. When aqueous based adhesives are used, the invention detects and measures the presence of the adhesive on a substrate by measuring the absorption of near infrared energy at specific wavelengths. The specific wavelengths of interest are those where there is an absorption band for water and a second wavelength where there is no absorption band for water.

The substrate is monitored by the filtered detectors 34, 36, which are used to measure the absorption of near infrared energy on the substrate. When adhesive is present upon the substrate, the detector that is filtered to the absorption band of water detects a decrease in signal strength. The second detector, however, sees no change in signal. A differential measurement of absorption of near infrared energy is used to discriminate the adhesive from its substrate. The differential signal between the two detectors may be used to quantify the moisture content of the substrate and adhesive by offsetting one signal from the other.

The near infrared light source 28 is guided to collection optics 4 of the optical module 2. The collection optics 4 is exemplified by the lens assembly that uses the fiber optics 6 such as the trifurcated fiber optic bundle. Both the lens assembly and the trifurcated fiber optic bundle are transmissive in the near infrared region.

The trifurcated fiber optic bundle consists of fibers coming from the two filtered detectors 34, 36 and the near infrared light source 28. The fibers are combed so as to evenly distribute the light source and detectors within the trifurcated fiber bundle.

The lens assembly focuses the near infrared light at the focal length of the lens and collects reflected light energy, which is returned to the detectors. The detectors 34, 36 used are exemplified by high quality extended wavelength indium gallium arsenide photodiodes for use in the wavelength range from 800 nm to 2600 nm, but may instead be detectors such as lead sulfide, lead selenide, indium antimonide or indium arsenide. The indium gallium arsenide (InGaAs) is preferred due to its stability at room temperature and speed of response.

The detector that is used to inspect for presence of moisture is passband filtered at 1900 nm and is exemplified by the J18 Series InGaAs photodiodes (extended wavelength) manufactured by EG&G Judson of Montgomeryville, Penn. Other water absorption bands in the near infrared region could be used as well. The background reference detector may be a passband filtered at 1720 nm. Other non aqueous absorption bands in the near infrared region may be used as well.

Figure 3:
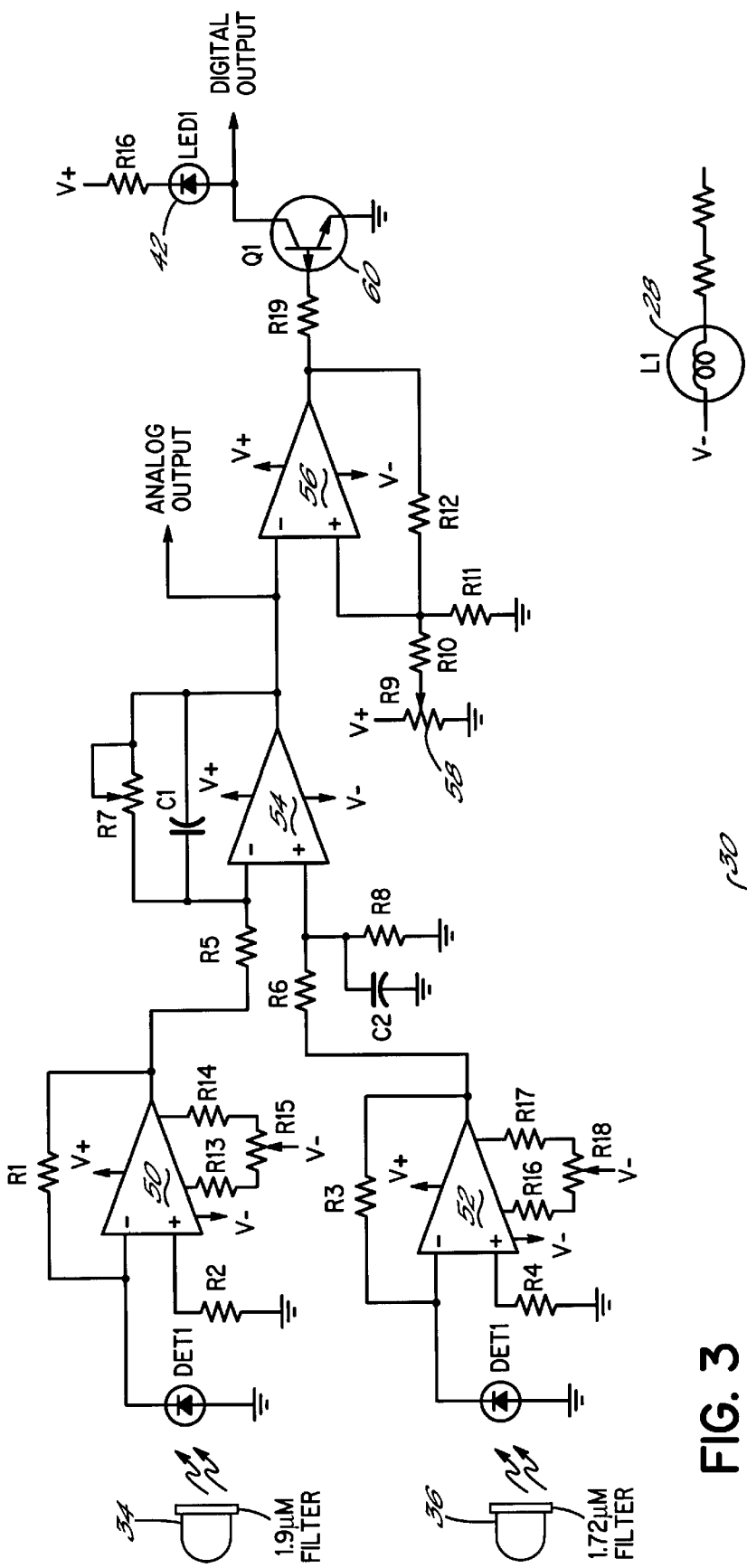
FIG. 3 is a schematic diagram of amplifier electronics for use in the glue detection apparatus of FIG. 2.

The signal processing electronics 18 of FIGS. 1 and 2 is exemplified by the amplifier electronics of FIG. 3. Transimpedence amplifier (current mode) preamplifiers 50, 52 are used to convert the current output of the InGaAs detectors into a voltage output. They amplify the signal for subsequent use by an offset device such as a differential amplifier 54.

When no moisture is present, the sensors generate outputs that pass through preamplifiers 50, 52 and are nearly equal. Thus, when such outputs are fed into the differential amplifier 54, the ensuing differential output of the differential amplifier 54 is nearly 0 volts, indicative of the condition where no moisture is present.

When moisture is present, the filtered detector 34 produces an output of smaller magnitude than that of the filtered detector 36 due to the adsorption of energy (within the absorption band of water) at its filtered wavelength. The differential amplifier 54 amplifies the difference in detector voltages, which is proportional to moisture content. The analog output is a negative voltage whose magnitude is proportional to detected moisture.

A voltage comparator 56 is used to digitize the analog glue/moisture signal and whose switching threshold is set by a resistor 58 to the moisture content of the adhesive to be detected and is higher than background levels of moisture content. By relying on this threshold as a cut-off level, there is no need to further compensate for moisture levels in the background, unlike conventional techniques.

The output of the voltage comparator 56 is buffered by a transistor 60, which serves as a driver to external devices. These external devices may then be driven by the transistor 60 to take corrective measures or other action with respect to the deposition of adhesive on the substrate. The output indicator 42 may be in the form of a light emitting diode.

If no adhesive is detected where the adhesive is supposed to be, appropriate external devices that control the deposition of adhesive may be triggered by the transistor 60 to deposit the adhesive in the area where the adhesive was supposed to be but was detected as missing, thereby correcting irregularities of adhesive deposition. Such external devices are conventional.

For those applications where sensing the presence or absence of the adhesive from a given area on a substrate does not go far enough to ensure uniformity of the adhesive in all areas or meet desired amounts, the detected moisture content may be used instead. Since the moisture content detected is indicative of the amount of adhesive present in a sensed region of the substrate, irregularities in the evenness of the adhesive present may be corrected by appropriate external devices triggered by the transistor 60, based on signals indicative of the sensed moisture content.

Figure 4:
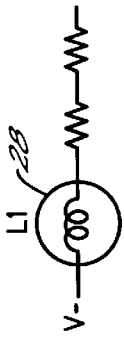
FIG. 4 is a schematic diagram of a power supply shown in box form in FIG. 1 for use to power the glue detection apparatus of FIG. 2.
Figure 5:
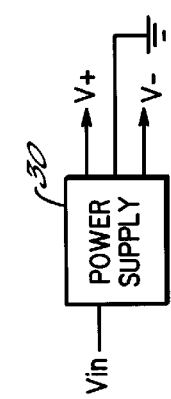
FIG. 5 is a schematic diagram of a near infrared light source shown in box form in FIG. 1 for use in generating near infrared light energy.

FIG. 3 shows various electronic components such as resistors, capacitors, voltage sources, diodes and grounds arranged in the circuitry to provide an operative circuit in accordance with conventional techniques. FIGS. 4 and 5 show circuits for the power supply and light in accordance with conventional techniques. The circuit components and their arrangement in FIGS. 3–5 that are ancillary to the detectors 34, 36, amplifiers 50, 52, differential amplifier 54, voltage comparator 56, output indicator 42, power supply 30, and near infrared light source 28 are conventional or readily apparent in accordance with conventional techniques to render operative the invention so that further description of such components would be superfluous information to what is known conventionally.

The glue sensor of FIG. 2 of the present application is commercially available from the VeriTec., Technologies, Inc., a wholly owned subsidiary of Nordson Corporation (Westlake, Ohio), model identification VeriTec GD 100 Glue Sensor and may be used for carton folder gluers, converting machinery, envelope machines, corrugated converting, mailers and folding machines, and any application requiring adhesive detection. Preferably, the present invention uses 1 mm glue spot resolution.

While the foregoing description and drawings represent the preferred embodiments of the present invention, it will be understood that various changes and modifications may be made without departing from the spirit and scope of the present invention.

What is claimed is:

1. An apparatus for on line detection and measurement of cold emulsion adhesives on a substrate, comprising:
   a sensor of a presence of an adhesive on a substrate, the sensor being arranged to sense an amount of absorption of two specific wavelengths of near infrared energy by the adhesive, the two specific wavelengths including a first wavelength within an absorption band for water and a second wavelength outside an absorption band for waters,
   a near infrared light source capable of emitting near infrared light,
   a lens assembly configured to focus near infrared light from said near infrared light source at a focal length of said lens assembly and to collect the near infrared light reflected from the substrate for return to the sensor, and
   signal processing electronics configured to continuously determine a quantitative reading of the moisture content from the amount of absorption by the substrate of said first and second wavelengths in the reflected near infrared light collected by said lens assembly and sensed by the sensor.

2. An apparatus as in claim 1, wherein the sensor includes a first selective light detector, and a second selective light detector, the first and second selective light detectors being arranged to detect light reflected from the substrate and collected by the lens assembly.

3. An apparatus as in claim 2, wherein said first and second selective light detectors are photodiodes whose composition includes materials selected from the group of indium gallium arsenide, lead sulfide, lead selenide, indium antimonide, indium arsenide, and combinations thereof.

4. An apparatus as in claim 2, further comprising a first and a second filter arranged with a respective one of said first and second selective light detectors to passband filter the wavelenghts of reflected light before the reflected light is detected by said first and second selective light detectors.

5. An apparatus as in claim 4, wherein said first and second filters filter the reflected light to transmit a passband of wavelenghts centered within a range of 800 nm to 2600 nm.

6. An apparatus as in claim 4, wherein said first filter is configured to passband filter the reflected light to provide a first passband of wavelenght for detection by said first selective light detector to provide a first measurement, and said second filter is configured to passband filter the reflected light to provide a second passband of wavelengths centered about the second wavelength for detection by said second selective light detector to provide a second measurement, and said signal processing electronics processes said first and second measurements to provide a continuous, quantitative reading indicative of the moisture content in the adhesive.

7. An apparatus as in claim 6, wherein said first wavelength is about 1900 nm and said second wavelength is about 1720 nm.

8. An apparatus as in claim 6, wherein said signal processing electronics is configured to offset said first and second measurements to the extent they exceed a threshold beneath which level is indicative of a moisture content of background sources.

9. An apparatus as in claim 6, wherein said first and second measurements are a first and a second current output, respectively, and said signal processing electronics comprises amplifiers arranged to convert said current first and second outputs into corresponding first and second voltage outputs and amplify the same and a differential amplifier arranged to receive the amplified first and second voltage outputs, said differential amplifier being configured to generate an output of about zero in response to no moisture content being sensed by said first selective light detector and to generate an output that is an amplification of a difference in said first and second voltage outputs that provides a quantitative reading from said selective light detectors in proportion to the sensed moisture content.

10. A method for on line detection and measurement of cold emulsion adhesives on a substrate, comprising:
    focusing near infrared light onto the substrate,
    collecting near infrared light that reflects back from the substrate,
    sensing an amount of absorption of two specific wavelengths of near infrared energy in the reflected near infrared light, the two specific wavelengths including a first wavelength within an absorption band for water and a second wavelength outside an absorption band for water, and
    continuously determining a quantitative reading of the moisture content from the amount of absorption of said first and second wavelengths sensed in the reflected near infrared light collected and sensed.

11. A method as in claim 10, wherein the sensing further comprises
    transmitting the reflected light to a first and a second selective light detector, and
    detecting the first and second wavelengths in the reflected light with the first and second selective light detectors, respectively.

12. A method as in claim 11, further comprising, before detecting the reflected light,
    filtering the reflected light reaching the first selective light detector for providing a first passband of wavelengths centered at the first wavelength within the absorption band for water, and
    filtering the reflected light reaching the second selective light detector for providing a second passband of wavelengths centered at the second wavelength outside the absorption band for water.

13. A method as in claim 12, wherein the first and second wavelengths of the reflected light are within a range of 800 nm to 2600 nm.

14. A method as in claim 12, wherein the first wavelength is 1900 nm and the second wavelength is 1720 nm.

15. A method as in claim 11, wherein the sensing further comprises detecting and filtering reflected light at the first wavelength to provide a first measurement, and detecting and filtering reflected light at the second wavelength to provide a second measurement, and the determining comprises offsetting the first and second measurements from each other to provide a reading indicative of the presence of moisture in the adhesive.

16. A method as in claim 15, wherein the offsetting of the first and second measurements to the extent they exceed a threshold beneath which level is indicative of a moisture content of background sources.

17. A method as in claim 15, further comprising:
    converting the first and second measurements from current outputs into voltage outputs,
    amplifying the voltage outputs, passing the amplified voltage outputs to a differential amplifier,
    generating an output from the differential amplifier of about zero in response to no moisture content being sensed by the first selective light detector, and
    generating a reading from the differential amplifier that is an amplification of a difference in the voltage outputs in proportion to the sensed moisture content.

* * * * *

UNITED STATES PATENT AND TRADEMARK OFFICE
CERTIFICATE OF CORRECTION

PATENT NO. : 6,281,500 B1
DATED : August 28, 2001
INVENTOR(S) : Martin A. Gaon

It is certified that error appears in the above-identified patent and that said Letters Patent is hereby corrected as shown below:

Column 4,
Line 48, change "waters," to -- water, --.

Column 5,
Line 15, change "wavelenght" to -- wavelengths --.
Line 15, after "wavelengths" insert -- centered about the first wavelength --.

Signed and Sealed this

Twentieth Day of August, 2002

Attest:

Attesting Officer

JAMES E. ROGAN
Director of the United States Patent and Trademark Office